United States Patent [19]

Cohen

[11] Patent Number: 4,795,527
[45] Date of Patent: Jan. 3, 1989

[54] TOOTH ETCHING

[76] Inventor: Howard Cohen, 339 Forest Ave., Woodmere, N.Y. 11598

[21] Appl. No.: 129,592

[22] Filed: Dec. 7, 1987

[51] Int. Cl.[4] .......................... B44C 1/22; C03C 15/00; C03C 25/06
[52] U.S. Cl. .................................... 156/629; 156/633; 156/635; 156/654; 156/345; 252/79.2
[58] Field of Search ............... 156/629, 633, 635, 654, 156/659.1, 345; 433/226, 229; 252/79.2

[56] References Cited

U.S. PATENT DOCUMENTS 2,067,925  1/1937  Clayton-Kennedy ............. 252/79.3
3,664,913  5/1972  Ratcliff .......................... 156/240 X Primary Examiner—William A. Powell
Attorney, Agent, or Firm—Robert W. Fiddler

[57] ABSTRACT

A method and means facilitating the application of etching agents to a tooth surface for bonding, laminating or the like dental processes. A manually manipulable matrix of a relatively flexible absorbent material dimensioned to correspond to a tooth surface to be treated is provided. This matrix is impregnated with any suitable etchant. A carrier handle is provided which may be formed integrally with or secured to the matrix. In use, positioning of the etchant impregnated matrix adjacent to the surface to be bonded insures the desired application of etchant to the tooth area to be etched.

22 Claims, 1 Drawing Sheet

TOOTH ETCHING

BACKGROUND OF INVENTION

This invention relates to the art of tooth etching, and more particularly to an improved method and means for applying desired etching agents to a tooth surface in an effective, precise and simple manner.

A variety of dental techniques have been evolved over the years in which a tooth surface to be treated is etched by the application of various etching agents such as phosphoric acid or the like to the tooth surface to provide desired surface roughening so as to implement the subsequent adhesion of a protective layer such as a bonding or laminate material; or the securement of an orthodontic attachment.

In etching a tooth surface to roughen it and thereby increase the available surface contact area to enhance the subsequent adhesion of some other material to the tooth surface, the etchant is generally applied by dabbing an impregnated swab material on the tooth. The swab is dipped into the etchant and then the etchant impregnated swab is positioned over the tooth surface. In the process, the quantity of etchant carried by the swab, if excessive, washes over onto adjacent teeth or teeth areas which it is not desired to etch, or onto adjacent soft tissue which may be burned. Alternatively, where the quantity of etchant material on the swab is kept to a minimum to eliminate overflow onto adjacent areas, the quantity of etchant is often insufficient to affect desired results. Further, the manipulation of the swab requires a great deal of care, so as to insure application of the etchant to the precise area to be treated.

BRIEF DESCRIPTION OF INVENTION

It is with the above problems and considerations in mind that the present improved etchant application method and means have been evolved, serving to implement the precise positioning of a required quantity of etchant on a tooth surface with minimum effort on the part of the user.

It is accordingly among the primary objectives of this invention to provide an improved method of applying etchant to a tooth surface.

Another object of the invention is to provide an improved etchant applicator, facilitating the application of etching material to a tooth surface.

It is also an object of the invention to provide means including both method and apparatus for applying an etching agent to a tooth surface without overflow of the etching agent to surrounding tooth and flesh areas which it is not desired to etch.

Another object of the invention is to provide means including both method and apparatus for accurately applying etchant to a tooth surface.

It is also an object of the invention to control the amount of etchant applied to a tooth surface to be etched.

These and other objects of the invention which will become hereafter apparent are achieved by providing a matrix dimensioned to approximate the size of a tooth surface. This matrix is then impregnated with an etchant, which may either be a liquid, a gel or in an actuatable dry form. A carrier handle member is preferably provided extending from the matrix to facilitate manipulation.

A feature of the invention resides in the fact that etchant impregnated matrices may be prepackaged for use as desired.

BRIEF DESCRIPTION OF THE DRAWINGS

The specific details of a preferred embodiment of the invention and the best mode for making and using it will be described in clear, concise, and exact terms, so as to enable those skilled in the art to practice the invention in connection with the accompanying drawings, wherein.

DESCRIPTION OF PREFERRED EMBODIMENTS

Figure 1:
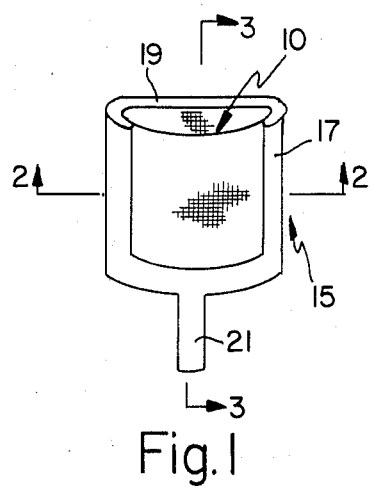
FIG. 1 is a perspective view on an enlarged scale of an etchant impregnated matrix made in accordance with the teachings of the inventions.

As best seen in the drawings, etchant impregnated matrix 10 (shown on an enlarged scale for purposes of clarity) is provided, dimensioned of a size and contour to permit its ready application against the surface of a conventional tooth. As will be understood by those skilled in the art, several different matrix sizes may be provided. However, the similarity in tooth size is such that tooth sizes for both children and adults will be probably be found sufficient to accomodate the range of variations in tooth size normally encountered.

The matrix 10 is formed of a resilient porous material, such as any one of a variety of foamed, relatively inert plastics such as polyurethane, polystyrene, or the like; sponge rubber; natural or synthetic textile fiber; paper; cellulose; or the like material lending itself to fabrication into a resilient liquid absorbing pad.

A carrier handle element 15 is preferably secured to the matrix. This carrier handle element 15 may be formed integrally with the matrix, or provided as part of a holder supporting the matrix.

Figure 2:
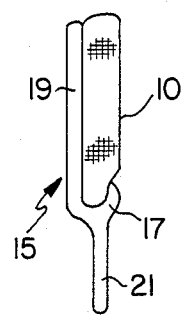
FIG. 2 is a transverse cross-sectional view through the matrix on line 2—2 of FIG. 1.
Figure 3:
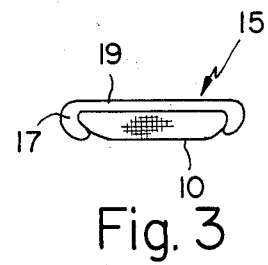
FIG. 3 is a longitudinal cross-sectional view on line 3—3 of FIG. 1.

In the embodiment illustrated in FIGS. 1–3, the carrier handle element 15 is shown formed with a three-sided frame portion 17, and backing plate 19, with a finger grip 21 at the closed end of the frame.

Any of a large variety of etchants may be employed to impregnate the matrix. Etchants such as a 2%-50% phosphoric or phosphorous acid solution in water have been found satisfactory. Similarly, phosphoric or phosphorous acid gels in fumed silica, or dry phosphoric or phosphorous anhydrides in a powder or crystaline form actuable by wetting may be employed.

Figure 4:
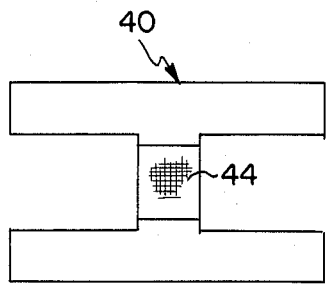
FIG. 4 is a plan view of another embodiment of the invention showing an H-shaped strip forming a carrier handle supporting an etchant impregnated matrix for treating a top occlusal tooth surface.
Figure 5:
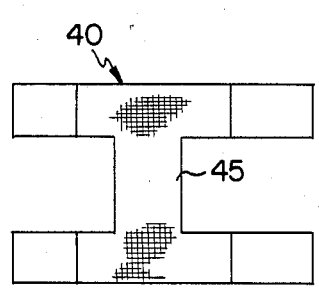
FIG. 5 is a plan view of an H-shaped carrier strip with impregnated matrix areas for treating top and sides of a tooth.
Figure 6:
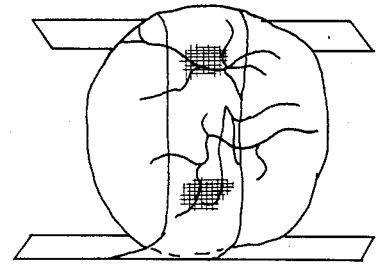
FIG. 6 is a view of an end occlusal tooth surface showing a strip of the type illustrated in FIGS. 4 and 5 applied to etch this occlusal surface.

In the embodiments of the invention shown in FIGS. 4, 5 and 6 as is apparent to those skilled in the art, a carrier handle 40 is shown formed of an H-shaped strip, which is formed of a flexible sheet material, which may either be absorbent or non-absorbent. Where non-absorbent, sheet material such as sheet vinyl or the like may be employed to which is secured an absorbent matrix formed of a material as above described, illustratively shown as formed of an rectangular pad 44 in FIG. 4 or an H-shaped pad 45 in FIG. 5.

Figure 7:
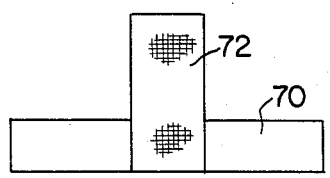
FIG. 7 is a top plan view of a T-shaped carrier handle with a central etching impregnated matrix.

FIG. 7 shows another embodiment in which a T-shaped carrier strip is employed formed of a material like the H-shaped carrier of FIGS. 4 and 5, provided with a rectangular matrix 67 like matrices 10, 44 and 45 suitable for positioning to contact the end and either front or rear face of a tooth.

Figure 8:
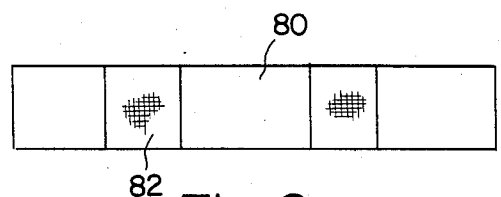
FIG. 8 is a top plan view of an elongate carrier handle strip with spaced etchant impregnated matrices, the strip being suitable for selective separation.
Figure 9:
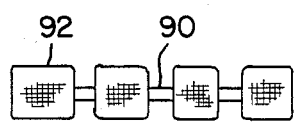
FIG. 9 is a top plan view of another form of elongate carrier strip supported matrices subject to selective separation.
Figure 10:
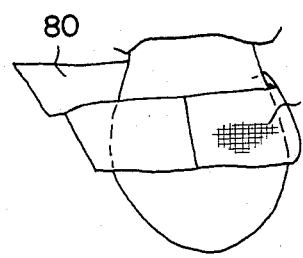
FIG. 10 is an elevational view of a tooth showing an interproximal surface being etched with a section of the strip of FIG. 8.

In the embodiments of the invention shown in FIGS. 8 and 9, a plurality of spaced etchant impregnated matrices (82 on FIG. 8, and 92 on FIG. 9) are supported by an elongate flexible carrier handle strip 80 in FIG. 8 and strip 90 in FIG. 9. Carrier handle strips 80 or 90 may, as in the FIGS. 4–7 embodiments, be formed of a non-absorbent sheet material such as sheet vinyl, to which spaced absorbent etchant impregnated pads (82 on FIG. 8 and 92 on FIG. 9) of absorbent material as above described such as cotton, sponge or the like are secured. In the FIGS. 8 and 9 embodiments, the carrier strip or handle 80 or 90 may alternatively be formed of a sheet material of woven or felted textile fibers such as cotton, or a combination of cotton and synthetic fibers with spaced areas etching impregnated (and preferably less tightly woven or compacted) to form the matrices 82 and 92.

Figure 11:
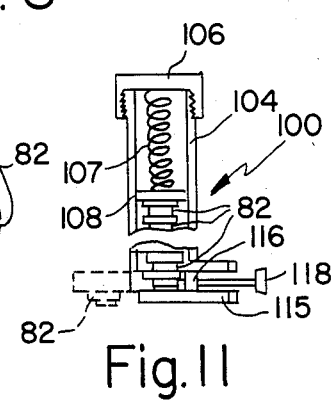
FIG. 11 is a schematic cross-sectional view, in broken section, showing a suggested manual dispenser for retaining and dispensing individual impregnated matrices.

A dispenser 100 is schematically depicted in FIG. 11 of a type which may be employed for storing and selectively dispensing individual matrices. The dispenser 100 is illustratively shown as containing a plurality of stacked matrices in a chamber 104, preferably of a cross-section to accomodate the shape of the matrices to be dispensed. A cap 106 closes the upper end of chamber 104, and a spring 107 has one end secured to cap 106 and the other end to plate 108, which rides in chamber 104 against the upper end of a stack of matrices such as 82. Spring-pressed plate 108 presses against matrices 82 to force them down to the lower dispensing end of the chamber. At this dispensing end, a discharge slideway 115 is formed with a spring-pressed plunger 116 arranged to move laterally with respect to the chamber axis, so that the application of pressure to plunger handle 118 acts to displace plunger 116 against the lowest matrix 82 in the stack of matrices in the chamber 104 to force this lowest matrix out of the discharge end of the dotted position shown to the dotted line position shown to the left in FIG. 11.

OPERATION

The above described structures as will be apparent to those skilled in the art may be formed employing a variety of production techniques such as conventionally employed in fabricating absorbent flexibile sheets, pads or swabs to form the desired matrix of desired contour and dimension.

Similarly, conventional production techniques may be employed to form the carrier handles, which may be formed separately of sheet materials, cut or otherwise formed to desired shape. The matrices may as described be either formed integrally with the carrier handle, or formed separately and subsequently secured thereto.

Thus, the matrix 10 of the FIGS. 1-3 embodiment, preferably with a handle element 15 is provided formed by any conventional foam forming techniques. Where battings of cotton, paper fibers or cellulose are employed, they may be pre-cut by conventional cutting or stamping techniques into a desired contour. The carrier handle, under such circumstances, may be formed either of a compressed edge of the matrix material, or by securing to the matrix a simple preformed plastic handle.

It is contemplated that production of the handled matrix of the FIGS. 1-3 embodiment may readily be accomplished by forming a mold which will form desired resilient porous material into a desired shape with a handle simultaneously by stamping sheet foamed polystyrene or polyurethane with simultaneous compression of a handle area from the foamed material.

Thereafter, the formed matrix is impregnated with the desired etchant, which as noted may comprise 2-50% phosphoric or phosphorous acid solution in water, or such other dilutant as may be desired; or phosphoric or acid gels, or dry phosphoric or phosphorous anhydrides in a water actuatable crystaline or powder form.

The etchant impregnated matrix 10 may be applied to a tooth surface by gripping the carrier handle and bringing the matrix up against the tooth surface to be treated. Thereafter, sufficient pressure is applied to the matrix against the tooth surface to be etched to release the etchant onto the tooth surface, after which the matrix may be removed.

The embodiments illustrated in FIGS. 4–10 may be satisfactorily formed with carrier handles of either absorbent or non-absorbent sheet materials with absorbent matrices.

Where the carrier handle is non-absorbent, the carrier handle may be suitably formed of a sheet material such as sheet vinyl cut to desired contour, H-shaped as in FIGS. 4 and 5; T-shaped as in FIG. 7; or as an elongate strip as in FIGS. 9 and 10. The matrix is formed of an absorbent flexible material such as a woven or felted synthetic or natural fiber, or a formed plastic or sponge rubber, or the like dimensioned of a size to fit over a tooth surface to be etched, and these matrices are secured to the carrier handle, arranged as illustrated and above described.

As is apparent to those skilled in the art, a combined matrix and handle may be formed utilizing the same materials for both matrix and carrier handle. Thus, felted or woven textile fibers may be formed with areas of higher absorbency to form the combined matrix and handle, or a formed plastic may be simultaneously cut and compressed in spaced areas to form the matrix and carrier as a unit.

In distribution, it is contemplated that a package of etchant impregnated matrices will be provided to the dentist, eliminating the need for storing etchants and applicators, and providing a readily available matrix of proper dimension with requisite amount of etchant ready for use.

The matrices may also be distributed by packaging them in a dispenser of the type shown in FIG. 11, so as to facilitate application to a surface either manually or mechanically.

In use, as is apparent, the etchant impregnated matrix is positioned over the tooth surface to be etched. Sufficient pressure is applied to release the etchant from the matrix, and the carrier and matrix are removed, as desired, after sufficient etchant has been applied and/or sufficient time has passed to attain desired etching. The etchant impregnated matrices may also be brought to a position adjacent the tooth surfaces by utilizing a dispenser of the type shown in FIG. 11, in which case, application of pressure to the plunger handle 118 will release a matrix for use on the tooth surface.

The above disclosure has been given by way of illustration and elucidation and not by way of limitation and it is intended to protect all embodiments of the invention within the scope of the appended claims.

I claim:

1. Etchant applying means for applying an etchant to a tooth, said applying means comprising: an absorbent resilient matrix dimensioned to approximate the size of the tooth surface to which the etchant is to be applied; and an etchant impregnated in said matrix of a quantity sufficient to coat the surface to effect desired etching upon the application of pressure to the matrix against the surface.

2. Etchant applying means as in claim 1 in which a carrier handle is secured to said matrix.

3. Etchant applying means as in claim 2 in which said carrier handle comprises a three-sided frame member lying along at least three sides of said matrix.

4. Etchant applying means as in claim 2 in which said handle comprises a backing plate formed against a matrix surface opposed to that to be positioned against the tooth surface to be treated.

5. Etchant applying means as in claim 2 in which said handle comprises: a backing plate; a three-sided frame portion upstanding from three sides of said backing plate along three edges of said matrix; and a finger grip extending from said frame.

6. Etchant applying means as in claim 5 in which said matrix is formed of a foamed polymer; and said carrier handle is molded simultaneously with the matrix.

7. Etchant applying means as in claim 1 in which said matrix is formed of a resilient absorbent material selected from a group consisting of: foamed plastics, sponge rubber; paper; cellulose; woven textile fibers; and felted textile fibers.

8. Etchant applying means as in claim 1 in which said etchant comprises: an aqueous solution of 2%-50% phosphoric acid.

9. Etchant applying means as in claim 1 in which said etchant comprises a phosphoric acid in fumed silica.

10. Etchant applying means as in claim 1 in which said etchant is selected from the group consisting of: phosphoric acid; phosphorous acid; phosphoric anhydride; and phosphorous anhydride.

11. Etchant applying means as in claim 10 in which said anhydrides are crystaline.

12. Etchant applying means as in claim 2 in which said carrier handle is of an H-shaped configuration.

13. Etchant applying means as in claim 12 in which said matrix is of an H-shaped configuration overlying the cross-bar and part of the legs of the H-shaped carrier.

14. Etchant applying means as in claim 2 in which said carrier handle is of a T-shaped configuration.

15. Etchant applying means as in claim 2 in which said carrier handle is shaped as an elongate strip.

16. Etchant applying means as in claim 15 in which a plurality of matrices are arranged at spaced points to said carrier handle.

17. Etchant applying means as in claim 16 in which said matrices are positioned to extend beyond the opposed longitudinally extending edges of the strip forming said carrier handle.

18. Etchant applying means as in claim 2 in which said carrier handle and said matrix are formed integrally of the same material with said carrier handle being denser than said matrix.

19. A method of applying an etchant to a tooth surface comprising the steps of: forming an absorbent matrix dimensioned to approximate the size of a tooth face; impregnating the matrix with an etchant; positioning the matrix in contact with the tooth surface to be etched; applying sufficient pressure to the matrix against the tooth surface to release the etchant; and removing the matrix.

20. A method as in claim 19 in which a laminate is secured to the etched tooth surface.

21. A method as in claim 19 in which the matrix is delivered to the point where positioning in contact with a tooth surface is desired by means of a dispenser.

22. A package of etchant impregnated matrices as in claim 1.

* * * * *